United States Patent [19]

Waterson

[11] Patent Number: 5,298,511
[45] Date of Patent: Mar. 29, 1994

[54] ALKANOIC ACID DERIVATIVES

[75] Inventor: David Waterson, Bollington, England

[73] Assignees: Imperial Chemical Industries PLC, London, United Kingdom; I.C.I. Pharma, Cedex, France

[21] Appl. No.: 948,594

[22] Filed: Sep. 23, 1992

[30] Foreign Application Priority Data

Oct. 3, 1991 [EP] European Pat. Off. ........ 91402638.0

[51] Int. Cl.$^5$ .................. C07D 215/14; C07D 215/16; C07C 69/76; C07C 315/00; C07C 321/00
[52] U.S. Cl. ..................... 514/311; 546/174; 546/155; 560/10; 560/56; 562/466; 562/427
[58] Field of Search .................. 560/56, 10; 562/427, 562/466; 514/311

[56] References Cited

U.S. PATENT DOCUMENTS

| | | | |
|---|---|---|---|
| 4,772,703 | 9/1988 | Musser | 544/283 |
| 4,929,626 | 5/1990 | Mohrs et al. | 514/311 |
| 4,960,892 | 10/1990 | Kreft, III | 546/152 |
| 4,970,215 | 11/1990 | Mohrs et al. | 514/311 |
| 5,098,930 | 3/1992 | Edwards | 514/459 |
| 5,132,328 | 7/1992 | Girodeau | 514/716 |

FOREIGN PATENT DOCUMENTS

| | | |
|---|---|---|
| 2023829 | 2/1991 | Canada . |
| 0181568 | 5/1986 | European Pat. Off. . |
| 0200101 | 12/1986 | European Pat. Off. . |
| 0344519 | 12/1989 | European Pat. Off. . |
| 0385679 | 5/1990 | European Pat. Off. . |
| 0414076 | 2/1991 | European Pat. Off. . |

OTHER PUBLICATIONS

Honda et al, "Synthesis of (±)-Aphanorphine via an Aminylium Ion Intermediate", J. Chem. Soc. Perkin Trans. I, Mar. 1992, pp. 531–532.

*Primary Examiner*—Paul J. Killos
*Attorney, Agent, or Firm*—Cushman, Darby & Cushman

[57] ABSTRACT

The invention concerns alkanoic acid derivatives of the formula I

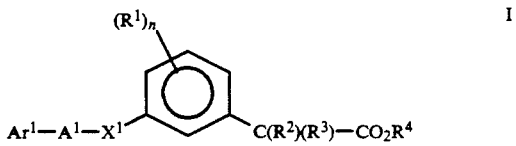

wherein $Ar^1$ is optionally-substituted phenyl or naphthyl, or a 10-membered bicyclic heterocyclic moiety containing one or two nitrogen heteroatoms and optionally containing a further heteroatom selected from nitrogen, oxygen and sulphur;
$A^1$ is a direct link to $X^1$ or is (1–3 C)alkylene;
$X^1$ is oxy, thio, sulphinyl or sulphonyl;
n is 0, 1 or 2 and $R^1$ is halogeno, (1–4 C)alkyl, (1–4 C)alkoxy or fluoro-(1–4 C)alkyl;
each of $R^2$ and $R^3$ is (1–4 C)alkyl, (2–4 C)alkenyl or (2–4 C)alkynyl; and
$R^4$ is hydrogen or (1–4 C)alkyl;
or a pharmaceutically-acceptable salt thereof;

processes for their manufacture; pharmaceutical compositions containing them and their use as 5-lipoxygenase inhibitors.

9 Claims, No Drawings

ALKANOIC ACID DERIVATIVES

This invention concerns alkanoic acid derivatives and more particularly alkanoic acid derivatives which are inhibitors of the enzyme 5-lipoxygenase (hereinafter referred to as 5-LO). The invention also concerns processes for the manufacture of said alkanoic acid derivatives and pharmaceutical compositions containing them. Also included in the invention is the use of said alkanoic acid derivatives in the treatment of various inflammatory and/or allergic diseases in which the direct or indirect products of 5-LO catalysed oxidation of arachidonic acid are involved, and the production of new medicaments for such use.

As stated above the alkanoic acid derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptide-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as inflammation of the joints (especially rheumatoid arthritis, oesteoarthritis and gout), inflammation of the gastrointestinal tract (especially inflammatory bowel disease, ulcerative colitis and gastritis), skin disease (especially psoriasis, eczema and dermatitis) and respiratory disease (especially asthma, bronchitis and allergic rhinitis), and in the production and development of various cardiovascular and cerebrovascular disorders such as myocardial infarction, angina and peripheral vascular disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

It is disclosed in European Patent Application No. 0181568 that 3-(2-quinolylmethoxy)phenylacetic acid and 2-[3-(2-quinolylmethoxy)phenyl]propionic acid and certain methyl or ethyl esters thereof possess anti-inflammatory properties.

It is further disclosed in European Patent Application No. 0344519 that certain 2-[4-(2-quinolylmethoxy)phenyl]acetic acid derivatives, wherein the 2-position of the acetic acid is mono-substituted with, for example, a cycloalkyl-alkyl group, are inhibitors of the enzyme lipoxygenase.

It is further disclosed in European Patent Application No. 0414076 that certain 2-[4-(2-quinolylmethoxy)phenyl]acetic acid derivatives, wherein the 2-position of the acetic acid is di-substituted with, for example, a but-1,4-diyl radical to form a cyclopentanecarboxylic acid derivative, are inhibitors of the enzyme lipoxygenase.

We have now discovered that certain novel phenylacetic acid derivatives wherein the 2-position of the acetic acid is di-substituted possess surprisingly potent 5-LO inhibitory activity. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided an alkanoic acid derivative of the formula I (set out hereinafter) wherein $Ar^1$ is phenyl or naphthyl, or a 10-membered bicyclic heterocyclic moiety containing one or two nitrogen heteroatoms and optionally containing a further heteroatom selected from nitrogen, oxygen and sulphur, and $Ar^1$ may optionally bear up to four substituents selected from halogeno, hydroxy, cyano, oxo, thioxo, (1–4 C)alkyl (1–4 C)alkoxy, fluoro-(1–4 C)alkyl, phenyl, benzoyl, phenyl-(1–4 C)alkyl and $\alpha,\alpha$-difluorobenzyl, and wherein said phenyl substituent or any of said substituents which contain a phenyl group may optionally bear a substituent selected from halogeno, (1–4 C)alkyl and (1–4 C)alkoxy;

$A^1$ is a direct link to $X^1$ or is (1–3 C)alkylene;

$X^1$ is oxy, thio, sulphinyl or sulphonyl;

n is 0, 1 or 2, and $R^1$ is halogeno, (1–4 C)alkyl, (1–4 C)alkoxy or fluoro-(1–4 C)alkyl;

each of $R^2$ and $R^3$, which may be the same or different, is (1–4 C)alkyl, (2–4 C)alkenyl or (2–4 C)alkynyl; and $R^4$ is hydrogen or (1–4 C)alkyl;

or a pharmaceutically-acceptable salt thereof.

According to a further feature of the invention there is provided an alkanoic acid derivative of the formula I wherein $Ar^1$, $A^1$, $X^1$, $R^1$, n and $R^4$ have any of the meanings defined hereinbefore and wherein each of $R^2$ and $R^3$, which may be the same or different, is (1–4 C)alkyl, (2–4 C)alkenyl, (2–4 C)alkynyl or fluoro-(1–4 C)alkyl; or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of the formula I defined above may exhibit the phenomenon of tautomerism and any formula drawing presented herein may represent only one of the possible tautomeric forms, the invention includes in its definition any tautomeric form of a compound of the formula I which possesses the property of inhibiting 5-LO and is not to be limited merely to any one tautomeric form utilised within the formulae drawings.

It is further to be understood that, insofar as certain of the compounds of formula I defined above may exist in optically active or racemic forms by virtue of one or more asymmetric carbon atoms, the invention includes in its definition any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for $Ar^1$ when it is naphthyl is, for example, 1-naphthyl or 2-naphthyl.

A suitable value for $Ar^1$ when it is a 10-membered bicyclic heterocyclic moiety containing one or two nitrogen heteroatoms and optionally containing a further heteroatom selected from nitrogen, oxygen and sulphur is, for example, a 10-membered benzo-fused heterocyclic moiety such as quinolyl, isoquinolyl, cinnolinyl, quinazolinyl, quinoxalinyl, 4 H-1,4-benzoxazinyl or 4 H-1,4-benzothiazinyl, or a hydrogenated derivative thereof such as 1,2-dihydroquinolyl, 1,2,3,4-tetrahydroquinolyl, 1,2-dihydroisoquinolyl, 2,3-dihydro-4 H-1,4-benzoxazinyl or 2,3-dihydro-4 H-1,4-benzothiazinyl. The heterocyclic moiety may be attached through any available position including from either of the two rings of the bicyclic heterocyclic moiety and including through an available nitrogen atom. The heterocyclic moiety may bear a suitable substituent such as, for example, a (1–4 C)alkyl, phenyl, benzoyl or phenyl-(1–4 C)alkyl substituent on an available nitrogen atom.

Suitable values for substituents which may be present on $Ar^1$, or on the phenyl substituent on $Ar^1$ or on any of the substituents on $Ar^1$ which contain a phenyl group, or suitable values for $R^1$ include, for example:

| | |
|---|---|
| for halogeno: | fluoro, chloro, bromo and iodo; |
| for (1–4C)alkyl: | methyl, ethyl, propyl, isopropyl, butyl, isobutyl, sec-butyl and tert-butyl; |
| for (1–4C)alkoxy: | methoxy, ethoxy, propoxy, isopropoxy and butoxy; |
| for fluoro-(1–4C)alkyl: | fluoromethyl, difluoromethyl, trifluoromethyl, 2-fluoroethyl, 2,2,2-trifluoroethyl and pentafluoroethyl; |
| for phenyl-(1–4C)alkyl: | benzyl, phenethyl, 3-phenylpropyl and α-methylbenzyl. |

A suitable value for $A^1$ when it is (1–3 C)alkylene is, for example, methylene, ethylene or trimethylene.

A suitable value for $R^2$, $R^3$ or $R^4$ when it is (1–4 C)alkyl is, for example, methyl, ethyl, propyl, isopropyl, butyl or tert-butyl; when it is (2–4 C)alkenyl is, for example, vinyl, allyl, prop-1-enyl, but-1-enyl, but-2-enyl, 2-methylprop-1-enyl or 2-methylprop-2-enyl; when it is (2–4 C)alkynyl is, for example, ethynyl, 1-propynyl or 2-propynyl; and when it is fluoro-(1–4 C)alkyl is, for example, fluoromethyl, 2-fluoroethyl or 2,2,2-trifluoroethyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular compounds of the invention are, for example, alkanoic acid derivatives of the formula I wherein:

(a) $Ar^1$ is phenyl or naphthyl which may optionally bear one, two or three substituents selected from any of those substituents on $Ar^1$ defined hereinbefore other than oxo and thioxo; and $A^1$, $X^1$, n, $R^1$, $R^2$, $R^3$ and $R^4$ have any of the meanings defined hereinbefore or in this section concerning particular compounds of the invention;

(b) $Ar^1$ is phenyl or naphth-2-yl which may optionally bear one or two substituents selected from fluoro, chloro, methyl, ethyl, isopropyl, tert-butyl, methoxy, trifluoromethyl, phenyl, benzoyl, benzyl and α,α-difluorobenzyl, and wherein said phenyl, benzoyl, benzyl or α,α-difluorobenzyl substituents may optionally bear a substituent selected from fluoro, chloro, methyl and methoxy; and $A^1$, $X^1$, n, $R^1$, $R^2$, $R^3$ and $R^4$ have any of the meanings defined hereinbefore or in this section concerning particular compounds of the invention;

(c) $Ar^1$ is a 10-membered benzo-fused heterocyclic moiety containing one or two nitrogen heteroatoms and optionally containing a further heteroatom selected from oxygen and sulphur, which heterocyclic moiety may optionally bear one or two oxo or thioxo substituents and up to two further substituents selected from any of those substituents on $Ar^1$ defined hereinbefore other than oxo or thioxo; and $A^1$, $X^1$, n, $R^1$, $R^2$, $R^3$ and $R^4$ have any of the meanings defined hereinbefore or in this section concerning particular compounds of the invention;

(d) $Ar^1$ is quinolyl, 1,2-dihydroquinolyl, isoquinolyl, 1,2-dihydroisoquinolyl, quinoxalinyl, 2,3-dihydro-4 H-1,4-benzoxazinyl or 2,3-dihydro-4 H-1,4-benzothiazinyl, which may optionally bear one or two oxo or thioxo substituents and up to two further substituents selected from any of those substituents on $Ar^1$ defined hereinbefore other than oxo or thioxo; and $A^1$, $X^1$, n, $R^1$, $R^2$, $R^3$ and $R^4$ have any of the meanings defined hereinbefore or in this section concerning particular compounds of the invention;

(e) $Ar^1$ is quinolyl, 1,2-dihydroquinolyl, 1,2,3,4-tetrahydroquinolyl or 2,3-dihydro-4 H-1,4-benzoxazinyl which may optionally bear one oxo or thioxo substituent and up to two further substituents selected from any of those substituents on $Ar^1$ defined hereinbefore other than oxo or thioxo; and $A^1$, $X^1$, n, $R^1$, $R^2$, $R^3$ and $R^4$ have any of the meanings defined hereinbefore or in this section concerning particular compounds of the invention;

(f) $Ar^1$ is 2-quinolyl, 3-quinolyl, 6-quinolyl, 7-quinolyl, 3-isoquinolyl, 6-isoquinolyl, 7-isoquinolyl, 2-quinoxalinyl, 6-quinoxalinyl, 4 H-1,4-benzoxazin-6-yl or 4 H-1,4-benzothiazin-6-yl, which may optionally bear one or two substituents selected from any of those substituents on $Ar^1$ defined hereinbefore other than oxo or thioxo; and $A^1$, $X^1$, n, $R^1$, $R^2$, $R^3$ and $R^4$ have any of the meanings defined hereinbefore or in this section concerning particular compounds of the invention;

(g) $Ar^1$ is 2-oxo-1,2-dihydroquinolinyl, 3-oxo-2,3-dihydro-4 H-1,4-benzoxazinyl or 3-oxo-2,3-dihydro-4 H-1,4-benzothiazinyl, or the corresponding thioxo derivatives thereof, which may optionally bear up to three substituents selected from any of those substituents on $Ar^1$ defined hereinbefore other than oxo or thioxo; and $A^1$, $X^1$, n, $R^1$, $R^2$, $R^3$ and $R^4$ have any of the meanings defined hereinbefore or in this section concerning particular compounds of the invention;

(h) $Ar^1$ is 2-oxo-1,2-dihydroquinolinyl, 2-thioxo-1,2-dihydro-quinolinyl, 2-oxo-1,2,3,4-tetrahydroquinolinyl, 2-thioxo-1,2,3,4-tetrahydroquinolinyl or 3-oxo-2,3-dihydro-4 H-1,4-benzoxazinyl which may optionally bear up to three substituents selected from any of those substituents on $Ar^1$ defined hereinbefore other than oxo or thioxo; and $A^1$, $X^1$, n, $R^1$, $R^2$, $R^3$ and $R^4$ have any of the meanings defined hereinbefore or in this section concerning particular compounds of the invention;

(i) $Ar^1$ is 2-oxo-1,2-dihydroquinolin-3-yl, 2-oxo-1,2-dihydroquinolin-6-yl, 2-oxo-1,2-dihydroquinolin-7-yl, 3-oxo-2,3-dihydro-4 H-1,4-benzoxazin-7-yl or 3-oxo-2,3-dihydro-4H-1,4-benzothiazin-7-yl, which may optionally bear up to three substituents selected from any of those substituents on $Ar^1$ defined hereinbefore other than oxo or thioxo; and $A^1$, $X^1$, n, $R^1$, $R^2$, $R^3$ and $R^4$ have any of the meanings defined hereinbefore or in this section concerning particular compounds of the invention;

(j) $A^1$ is a direct link to $X^1$, and $X^1$ is oxy, thio, sulphinyl or sulphonyl; and $Ar^1$, n, $R^1$, $R^2$, $R^3$ and $R^4$ have any of the meanings defined hereinbefore or in this section concerning particular compounds of the invention;

(k) $A^1$ is methylene and $X^1$ is oxy; and $Ar^1$, n, $R^1$, $R^2$, $R^3$ and $R^4$ have any of the meanings defined hereinbefore or in this section concerning particular compounds of the invention;

(l) n is 0 or 1 and $R^1$ is fluoro, chloro, methyl, methoxy or trifluoromethyl; and $Ar^1$, $A^1$, $X^1$, $R^2$, $R^3$ and $R^4$ have any of the meanings defined hereinbefore or in this section concerning particular compounds of the invention;

(m) each of $R^2$ and $R^3$, which may be the same or different, is methyl, ethyl, propyl, vinyl, allyl, ethynyl or 2-propynyl; and $Ar^1$, $A^1$, $X^1$, n, $R^1$ and $R^4$ have any of the meanings defined hereinbefore or in this section concerning particular compounds of the invention;

(n) each of $R^2$ and $R^3$, which may be the same or different, is methyl, ethyl, propyl, vinyl, allyl, ethynyl, prop-2-ynyl, fluoromethyl or 2-fluoroethyl; and $Ar^1$, $A^1$, $X^1$, n, $R^1$ and $R^4$ have any of the meanings defined hereinbefore or in this section concerning particular compounds of the invention; and (o) $R^4$ is hydrogen, methyl, ethyl, propyl, butyl or tert-butyl; and $Ar^1$, $A^1$, $X^1$, n, $R^1$, $R^2$ and $R^3$ have any of the meanings defined hereinbefore;

or a pharmaceutically-acceptable salt thereof.

A preferred compound of the invention comprises an alkanoic acid derivative of the formula I wherein $Ar^1$ is phenyl which may optionally bear a substituent selected from fluoro, chloro, methyl, tert-butyl, phenyl, benzoyl, benzyl and α,α-difluorobenzyl and wherein said phenyl, benzoyl, benzyl or α,α-difluorobenzyl substituent may optionally bear a fluoro or chloro substituent, or $Ar^1$ is naphth-2-yl which may optionally bear a substituent selected from fluoro, chloro and methyl;

$A^1$ is a direct link to $X^1$, or is methylene;

$X^1$ is oxy, thio, sulphinyl or sulphonyl;

n is 0 or 1 and $R^1$ is from fluoro, chloro or trifluoromethyl; each of $R^2$ and $R^3$, which may be the same or different, is methyl, ethyl, propyl, allyl or 2-propynyl;

$R^4$ is methyl, ethyl, propyl, butyl, or tert-butyl;

or a pharmaceutically-acceptable salt thereof.

A further preferred compound of the invention comprises an alkanoic acid derivative of the formula I wherein $Ar^1$ is 2-quinolyl, 6-quinolyl, 6-quinoxazinyl, 2-oxo-1,2-dihydroquinolin-3-yl, 2-oxo-1,2-dihydroquinolin-6-yl, 2-oxo-1,2-dihydroquinolin-7-yl, 3-oxo-2,3-dihydro-4 H-1,4-benzoxazin-7-yl or 3-oxo-2,3-dihydro-4 H-1,4-benzothiazin-7-yl, which may optionally bear one, two or three substituents selected from fluoro, chloro, methyl, ethyl and 2-fluoroethyl;

$A^1$ is a direct link to X or is methylene;

$X^1$ is oxy, thio, sulphinyl or sulphonyl;

n is 0 or 1 and $R^1$ is fluoro, chloro or trifluoromethyl;

each of $R^2$ and $R^3$, which may be the same or different, is methyl, ethyl propyl, allyl or 2-propynyl;

and $R^4$ is methyl, ethyl, propyl, butyl or tert-butyl;

or a pharmaceutically-acceptable salt thereof.

A further preferred compound of the invention comprises an alkanoic acid derivative of the formula I wherein $Ar^1$ is phenyl which may optionally bear a substituent selected from fluoro, chloro, methyl, tert-butyl, phenyl, benzoyl, benzyl and α,α-difluorobenzyl and wherein said phenyl, benzoyl, benzyl or α,α-difluorobenzyl substituent may optionally bear a fluoro or chloro substituent, or $Ar^1$ is naphth-2-yl which may optionally bear a substituent selected from fluoro, chloro and methyl;

$A^1$ is a direct link to $X^1$, or is methylene;

$X^1$ is oxy, thio, sulphinyl or sulphonyl;

n is 0 or 1 and $R^1$ is fluoro, chloro or trifluoromethyl;

each of $R^2$ and $R^3$, which may be the same or different, is methyl, ethyl or allyl;

and $R^4$ is methyl or ethyl;

or a pharmaceutically-acceptable salt thereof.

A further preferred compound of the invention comprises an alkanoic acid derivative of the formula I wherein $Ar^1$ is 2-quinolyl, 6-quinolyl, 2-oxo-1,2-dihydroquinolin-3-yl or 2-oxo-1,2-dihydroquinolin-6-yl, which may optionally bear one substituent selected from fluoro, chloro, methyl and ethyl; $A^1$ is a direct link to $X^1$, or is methylene;

$X^1$ is oxy, thio, sulphinyl or sulphonyl;

n is 0 or 1 and $R^1$ is fluoro, chloro or trifluoromethyl;

each of $R^2$ and $R^3$, which may be the same or different, is methyl, ethyl or allyl;

and $R^4$ is methyl or ethyl;

or a pharmaceutically-acceptable salt thereof.

A further preferred compound of the invention comprises an alkanoic acid derivative of the formula I wherein $Ar^1$ is naphth-2-yl, 2-quinolyl or 1-methyl-2-oxo-1,2-dihydroquinolin-6-yl;

$A^1$ is methylene and $X^1$ is oxy;

n is 0;

$R^2$ is methyl, ethyl or allyl;

$R^3$ is methyl or ethyl; and $R^4$ is methyl or ethyl;

or a pharmaceutically-acceptable salt thereof.

A specific especially preferred compound of the invention is the following compound of the formula I, or a pharmaceutically-acceptable salt thereof:

ethyl 2-ethyl-2-[3-(naphth-2-ylmethoxy)phenyl]butyrate, methyl 2-methyl-2-[3-(naphth-2-ylmethoxy)phenyl]propionate, ethyl 2-ethyl-2-[3-(2-quinolylmethoxy)phenyl]butyrate, ethyl 2-ethyl-2-[3-(1-methyl-2-oxo-1,2-dihydroquinolin-6-ylmethoxy)phenyl]butyrate,
ethyl 2-methyl-2-[3-(1-methyl-2-oxo-1,2-dihydroquinolin-6-yl-methoxy)phenyl]butyrate or
ethyl 2-allyl-2-[3-(1-methyl-2-oxo-1,2-dihydroquinolin-6-yl-methoxy)phenyl]butyrate.

A compound of the invention comprising an alkanoic acid derivative of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, $Ar^1$, $A^1$, $X^1$, n, $R^1$, $R^2$, $R^3$ and $R^4$ have any of the meanings defined hereinbefore.

(a) The coupling, preferably in the presence of a suitable base, of a compound of the formula II with a compound of the formula $Ar^1$-$A^1$-Z wherein Z is a displaceable group; provided that, when there is a hydroxy group in $Ar^1$ any hydroxy group may be protected by a conventional protecting group or alternatively any such group need not be protected, whereafter any undesired protecting group in $Ar^1$ is removed by conventional means.

A suitable displaceable group Z is, for example, a halogeno or sulphonyloxy group, for example a fluoro, chloro, bromo, iodo, methanesulphonyloxy or toluene-p-sulphonyloxy group.

A suitable base for the coupling reaction is, for example, an alkali or alkaline earth metal carbonate, (1–4 C)alkoxide, hydroxide or hydride, for example sodium carbonate, potassium carbonate, sodium ethoxide, potassium butoxide, sodium hydroxide, potassium hydroxide, sodium hydride or potassium hydride; or an organometallic base such as (1–4 C)alkyl-lithium, for example n-butyl-lithium.

The coupling reaction is conveniently performed in a suitable inert solvent, for example N,N-dimethylformamide, N,N-dimethylacetamide, N-methylpyrrolidin-2-one, dimethylsulphoxide, acetone, 1,2-dimethoxyethane or tetrahydrofuran, and at a temperature in the range, for example, 10° to 150° C., conveniently at or near 100° C.

The reaction may conveniently be performed in the presence of a suitable catalyst, for example a metallic catalyst, for example palladium(O) or copper(I) such as tetrakis(triphenylphosphine)palladium, cuprous chloride or cuprous bromide.

A suitable protecting group for a hydroxy group is, for example, an acyl group, for example a (2–4 C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formula $Ar^1$-$A^1$-Z and of the formula II may be obtained by standard procedures of organic chemistry. Starting materials of the formula II are obtainable by analogous procedures to those illustrated in the accompanying Examples or by modifications thereto which are within the ordinary skill of an organic chemist.

(b) The coupling, preferably in the presence of a suitable base as defined hereinbefore, of a compound of the formula $Ar^1$-$A^1$-$X^1$-H with a compound of the formula III wherein Z is a displaceable group as defined hereinbefore; provided that, when there is a hydroxy group in $Ar^1$, any hydroxy group may be protected by a conventional protecting group as defined hereinbefore or alternatively any such group need not be protected, whereafter any undesired protecting group in $Ar^1$ is removed by conventional means.

The coupling reaction is conveniently performed in a suitable inert solvent or diluent as defined hereinbefore, and at a temperature in the range, for example, 10° to 150° C., conveniently at or near 100° C.

Conveniently the reaction may be performed in the presence of a suitable catalyst as defined hereinbefore.

The preparation of starting materials of the formula $Ar^1$-$A^1$-$X^1$-H and of the formula III may be obtained by standard procedures of organic chemistry as illustrated in European Patent Application Nos. 0375404, 0385662, 0409413, 0420511, 0462813 and 0488602.

(c) The coupling of a compound of the formula $Ar^1$-$A^1$-$X^1$-Z wherein Z is a displaceable group as defined hereinbefore, or alternatively, when $X^1$ is a thio group, Z may be a group of the formula $Ar^1$-$A^1$-$X^1$-, with an organometallic reagent of the formula IV wherein M is an alkali metal or an alkaline earth metal such as lithium or calcium or M represents the magnesium halide portion of a conventional Grignard reagent; provided that, when there is a hydroxy group in $Ar^1$ any hydroxy group may be protected by a conventional protecting group as defined hereinbefore or alternatively any such group need not be protected, whereafter any undesired protecting group in $Ar^1$ is removed by conventional means.

The coupling reaction is conveniently performed in a suitable inert solvent as defined hereinbefore and at a temperature in the range, for example, −80° to +50° C., conveniently in the range −80° C. to ambient temperature.

The preparation of starting materials of the formula $Ar^1$-$A^1$-$X^1$-Z and of the formula IV may be obtained by standard procedures of organic chemistry as illustrated in European Patent Application Nos. 0375404, 0385662, 0409413, 0420511, 0462813 and 0488602.

(d) For the production of those compounds of the formula I wherein $X^1$ is a sulphinyl or sulphonyl group, the oxidation of a compound of the formula I wherein $X^1$ is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(e) For the production of those compounds of the formula I wherein $Ar^1$ bears an alkyl substituent on an available nitrogen atom, the alkylation of a compound of the formula I wherein $Ar^1$ bears a hydrogen atom on said available nitrogen atom.

A suitable alkylating agent is, for example, any agent known in the art for the alkylation of an available nitrogen atom, for example an alkyl halide, for example a (1–4 C)alkyl chloride, bromide or iodide, in the presence of a suitable base. A suitable base for the alkylation reaction is, for example, an alkali or alkaline earth metal carbonate, sodium hydroxide, potassium hydroxide, sodium hydride or potassium hydride. The alkylation reaction is preferably performed in a suitable inert solvent or diluent, for example N,N-dimethylformamide, dimethylsulphoxide, acetone, 1,2-dimethoxyethane or tetrahydrofuran, and at a temperature in the range, for example, 10° to 150° C., conveniently at or near ambient temperature.

(f) For the production of those compounds of the formula I wherein $Ar^1$ bears one or more thioxo substituents, the reaction of a compound of the formula I wherein $Ar^1$ bears one or more oxo substituents with a thiation reagent such that each oxo substituent is converted into a thioxo substituent; provided that, when there is a hydroxy group in $Ar^1$ any such group may be protected by a conventional protecting group as defined hereinbefore or alternatively any such group need not be protected, whereafter any undesired protecting group in $Ar^1$ is removed by conventional means.

A suitable thiation reagent is, for example, any agent known in the art for the conversion of an oxo group to a thioxo group such as, for example, 2,4-bis-(4-methoxyphenyl)-1,3-dithia-2,4-diphosphetane-2,4-disulphide (Lawesson's Reagent) or phosphorus pentasulphide. The thiation reaction is generally carried out with the required stoichiometric amount of thiation reagent in order to reduce the risk of damage to other functional groups. In general the reaction is carried out in a suitable solvent or diluent such as toluene, xylene or tetrahydrofuran and at a temperature, for example, at or near the reflux temperature of the solvent or diluent, that is in the range 65° to 150° C.

When a pharmaceutically-acceptable salt of a compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

As stated previously, the novel compounds of the formula I are inhibitors of the enzyme 5-LO. The effects of this inhibition may be demonstrated using one or more of the standard procedures set out below:

a) An in vitro assay system involving incubating a test compound with heparinised human blood, prior to challenge with the calcium ionophore A23187 and then indirectly measuring the inhibitory effects on 5-LO by assaying the amount of $LTB_4$ using specific radioimmunoassays described by Carey and Forder (F. Carey and R. A. Forder, Prostaglandins, Leukotrienes Med., 1986, 22, 57; Prostaglandins, 1984, 28, 666; Brit. J. Pharmacol. 1985, 84, 34 P) which involve the use of a protein-$LTB_4$ conjugate produced using the procedure of Young et alia (Prostaglandins, 1983, 26(4), 605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TxB_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

b) An ex vivo assay system, which is a variation of test a) above, involving administration to a group of rats of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

c) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in one or more of the above tests a)–c):

Test a): $IC_{50}$ ($LTB_4$) in the range, for example, 0.01–40 $\mu M$ $IC_{50}$ ($TxB_2$) in the range, for example, 40–200 $\mu M$;

Test b): oral $ED_{50}$ ($LTB_4$) in the range, for example, 0.1–100 mg/kg;

Test c): oral $ED_{50}$ ($LTB_4$) in the range, for example, 0.1–50 mg/kg.

No overt toxicity or other untoward effects are present in tests b) and/or c) when compounds of the formula I are administered at several multiples of their minimum inhibitory dose or concentration.

Thus, by way of example, the compound ethyl 2-ethyl-2-[3-(naphth-2-ylmethoxy)phenyl]butyrate has an $IC_{50}$ of 0.2 $\mu M$ against $LTB_4$ in test a). In general those compounds of the formula I which are particularly preferred have an $IC_{50}$ of <1 $\mu M$ against $LTB_4$ in test a).

These compounds are examples of compounds of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises an alkanoic acid derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is an alkanoic acid derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided an alkanoic acid derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a compound of the formula I will naturally vary according to the nature and severity of the conditions, the age and sex of the animal or patient and the route of administration, according to well known principles of medicine. As mentioned above, compounds of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises an alkanoic acid derivative of the formula I, or a pharmaceutically-acceptable salt thereof as defined hereinbefore, in conjunction or admixture with a cyclooxygenase inhibitory non-steroidal anti-inflammatory agent (such as those mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at ambient temperature, tha is in the range 18°-25° C. and under an atmosphere of an inert gas such as argon;

(iii) column chromatography (by the flash procedure) and medium pressure liquid chromatography (HPLC) were performed on Merck Kieselgel silica (Art. 9385) or Merck Lichroprep RP-18 (Art. 9303) reversed-phase silica obtained from E. Merck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques; unless otherwise stated, $CDCl_3$ solutions of the end-products of the formula I were used for the determination of the NM spectral data, chemical shift values were measured on the delta scale and the following abbreviations are used; s, singlet; d, doublet; t, triplet; m, multiplet;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after crystallisation from a conventional organic solvent such as ethanol, methanol, acetone, ether or hexane, alone or in admixture; and (viii) the following abbreviations have been used:

| THF | tetrahydrofuran; |
|---|---|
| DHSO | dimethylsulphoxide; |
| DMF | N,N-dimethylformamide; |
| DMA | N,N-dimethylacetamide. |

EXAMPLE 1

A mixture of 2-bromomethylnaphthalene (0.088 g), ethyl 2-ethyl-2-(3-hydroxyphenyl)butyrate (0.1 g), potassium carbonate (0.11 g) and DMF (1.5 ml) was stirred at ambient temperature for 18 hours. The mixture was partitioned between ethyl acetate and water. The organic phase was washed with brine, dried ($MgSO_4$) and evaporated. The residue was purified by column chromatography using a 10:3 v/v mixture of hexane and ethyl acetate as eluent. There was thus obtained ethyl 2-ethyl-2-[3-(naphth-2-ylmethoxy)phenyl]-butyrate (0.12 g, 80%) as an oil.

NMR Spectrum: 0.72 (t, 6 H), 1.14 (t, 3 H), 2.01 (m, 4 H), 4.08 (q, 2 H), 5.20 (s, 2 H), 6.88 (m, 3 H), 7.23 (m, 1 H), 7.48 (m, 3 H), 7.82 (m, 4 H).

The ethyl 2-ethyl-2-(3-hydroxyphenyl)butyrate used as a starting material was obtained as follows:

A mixture of 3-methoxyphenylacetic acid (10 g), concentrated sulphuric acid (0.56 ml) and ethanol (45 ml) was heated to reflux for 4 hours. The mixture was evaporated and the residue was partitioned between diethyl ether and water. The organic phase was washed with water and with a saturated sodium bicarbonate solution, dried ($MgSO_4$) and evaporated. There was thus obtained ethyl 3-methoxyphenylacetate (9.4 g, 81%).

n-Butyl-lithium (1.6M in hexane, 3.75 ml) was added dropwise to a stirred solution of di-isopropylamine (0.84 ml) in THF (20 ml) which had been cooled to $-78°$ C. The mixture was stirred at $-78°$ C. for 30 minutes, allowed to warm to $0°$ C. and stirred for 10 minutes and recooled to $-78°$ C. A solution of ethyl 3-methoxyphenylacetate (1.16 g) in THF (5 ml) was added and the mixture was stirred at $-78°$ C. for 1 hour. Ethyl iodide (0.94 g) was added and the mixture was stirred for 18 hours at ambient temperature. The mixture was partitioned between diethyl ether and water. The organic phase was washed with dilute aqueous hydrochloric acid solution and with brine, dried ($MgSO_4$) and evaporated. The residue was purified by column chromatography using a 5:2 v/v mixture of hexane and ethyl acetate as eluent. There was thus obtained ethyl 2-(3-methoxyphenyl)butyrate (1.06 g, 80%) as an oil. NMR Spectrum: 0.88 (t, 3 H), 1.21 (t, 3 H), 1.78 (m, 1 H), 2.08 (m, 1 H), 3.4 (t, 1 H), 3.79 (s, 3 H), 4.10 (m, 2 H), 6.82 (m, 3 H), 7.20 (m, 1 H).

The product so obtained was alkylated with ethyl iodide using an analogous procedure to that described in the preceding paragraph. There was thus obtained ethyl 2-ethyl-2-(3-methoxyphenyl)butyrate (0.75 g, 67%) as an oil.

NMR Spectrum: 0.66 (t, 6 H), 1.10 (t, 3 H), 1.95 (m, 4 H), 3.72 (s, 3 H), 4.05 (q, 2 H), 6.72 (m, 3 H), 7.15 (m, 1 H).

A solution of a portion (0.53 g) of the product so obtained in methylene chloride (30 ml) was cooled to $-78°$ C. and boron tribromide (1M in methylene chloride, 4.35 ml) was added. The mixture was stirred at $-78°$ C. for 4 hours and at ambient temperature for 16 hours. Ethanol (1 ml) was added and the mixture was washed with a saturated aqueous sodium carbonate solution and with brine, dried ($MgSO_4$) and evaporated. The residue was purified by column chromatography using a 10:3 v/v mixture of hexane and ethyl acetate as eluent. There was thus obtained ethyl 2-ethyl-2-(3-hydroxyphenyl)butyrate (0.34 g, 69%) as an oil.

NMR Spectrum: 0.73 (t, 6 H), 1.18 (t, 3 H), 2.02 (m, 4 H), 4.12 (q, 2 H), 6.73 (m, 3 H), 7.18 (m, 1 H).

EXAMPLE 2

The procedure described in Example 1 was repeated except that methyl 2-(3-hydroxyphenyl)-2-methylpropionate was used in place of ethyl 2-ethyl-2-(3-hydroxyphenyl)butyrate. There was thus obtained methyl 2-methyl-2-[3-(naphth-2-ylmethoxy)phenyl]propionate in 76% yield, m.p. $64°$-$66°$ C.

The methyl 2-(3-hydroxyphenyl)-2-methylpropionate used as a starting material was obtained from 3-methoxyphenylacetic acid by analogous procedures to those described in the portion of Example 1 which is concerned with the preparation of starting materials except that methanol was used in place of ethanol in the esterification step, methyl iodide was used in place of ethyl iodide in the alkylation steps and methanol was used in place of ethanol when the boron tribromide step was quenched. There was thus obtained the required starting material in 30% yield as an oil.

NMR Spectrum: 1.55 (s, 6 H), 3.65 (s, 3 H), 5.30 (broad s, 1 H), 6.71 (m, 1 H), 6.84 (m, 2 H), 7.20 (m, 1 H).

EXAMPLE 3

The procedure described in Example 1 was repeated except that 2-chloromethylquinoline hydrochloride was used in place of 2-bromomethylnaphthalene and that a further equivalent of potassium carbonate was added to neutralise the hydrochloride salt. There was thus obtained ethyl 2-ethyl-2-[3-(2-quinolylmethoxy)phenyl]-butyrate in 37% as a gum.

NMR Spectrum: 0.70 (t, 6 H), 1.15 (t, 3 H), 2.01 (m, 4 H), 4.08 (q, 2 H), 5.39 (s, 2 H), 6.83–6.92 (m, 2 H), 6.98

(m, 1 H), 7.22 (m, 1 H), 7.52–7.85 (m, 4 H), 8.07–8.24 (m, 2 H).

EXAMPLE 4

The procedure described in Example 1 was repeated except that 6-bromomethyl-1-methyl-1,2-dihydroquinolin-2-one (European Patent Application No. 0385662, Example 6, Note a.) was used in place of 2-bromomethylnaphthalene. There was thus obtained ethyl 2-ethyl-2-[3-(1-methyl-2-oxo-1,2-dihydroquinolin-6-ylmethoxy)phenyl]butyrate in 56% yield as a gum.

NMR Spectrum 0.7 (t, 6 H), 1.15 (t, 3 H), 1.7–2.15 (m, 4 H), 3.75 (s, 3 H), 4.1 (q, 2 H), 5.1 (s, 2 H), 6.72 (d, 1 H), 6.8–6.95 (m, 3 H), 7.18–7.28 (m, 1 H), 7.35 (d, 1 H), 7.6–7.7 (m, 3 H).

EXAMPLE 5

Using an analogous procedure to that described in Example 1, 6-bromomethyl-1-methyl-1,2-dihydroquinolin-2-one was reacted with ethyl 2-(3-hydroxyphenyl)-2-methylbutyrate to give ethyl 2-methyl-2-[3-(1-methyl-2-oxo-1,2-dihydroquinolin-6-ylmethoxy)phenyl]butyrate in 44% yield as a gum.

NMR Spectrum: 0.82 (t, 3 H), 1.17 (t, 3 H), 1.50 (s, 3 H), 1.85–2.15 (m, 2 H), 3.75 (s, 3 H), 4.12 (q, 2 H), 5.12 (s, 2 H), 6.7–6.96 (m, 4 H), 7.22–7.42 (m, 2 H), 7.58–7.72 (m, 3 H).

The ethyl 2-(3-hydroxyphenyl)-2-methylbutyrate used as a starting material was obtained using the procedures described in the portion of Example 1 which is concerned with the preparation of starting materials except that methyl iodide was used in place of ethyl iodide in the second alkylation step. The intermediate so obtained, ethyl 2-(3-methoxyphenyl)-2-methylbutyrate, gave the following characteristic NMR signals: 0.84 (t, 3 H), 1.19 (t, 3 H), 1.5 (s, 3 H), 1.85–2.15 (m, 2 H), 3.8 (s, 3 H), 4.13 (q, 2 H), 6.72–6.92 (m, 3 H), 7.21 (m, 1 H).

EXAMPLE 6

Using an analogous procedure to that described in Example 1, 6-bromomethyl-1-methyl-1,2-dihydroquinolin-2-one was reacted with ethyl 2-allyl-2-(3-hydroxyphenyl)butyrate to give ethyl 2-allyl-2-[3-(1-methyl-2-oxo-1,2-dihydroquinolin-6-ylmethoxy)phenyl]butyrate in 25% yield as a gum.

NNR Spectrum: 0.75 (t, 3 H), 1.16 (t, 3 H), 2.02 (m, 2 H), 2.75 (m, 2 H), 3.72 (s, 3 H), 4.10 (q, 2 H), 5.05 (m, 2 H), 5.10 (s, 2 H), 5.48 (m, 1 H), 6.72 (d, 1 H), 6.85 (m, 3 H), 7.22 (m, 1 H), 7.48 (d, 1 H), 7.65 (m, 3 H).

The ethyl 2-allyl-2-(3-hydroxyphenyl)butyrate used as a starting material was obtained using the procedures described in the portion of Example 1 which is concerned with the preparation of starting materials except that allyl bromide was used in place of ethyl iodide in the second alkylation step. The intermediate so obtained, ethyl 2-allyl-2-(3-methoxyphenyl)butyrate gave the following characteristic NMR signals: 0.76 (t, 3 H), 1.18 (t, 3 H), 2.05 (m, 2 H), 2.75 (m, 2 H), 3.80 (s, 3 H), 4.15 (q, 2 H), 5.15 (m, 2 H), 5.50 (m, 1 H), 6.80 (m, 3 H), 7.22 (m, 1 H).

CHEMICAL FORMULAE

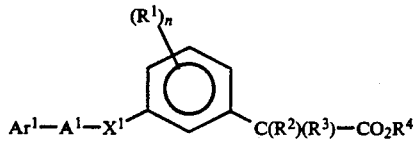

-continued
CHEMICAL FORMULAE

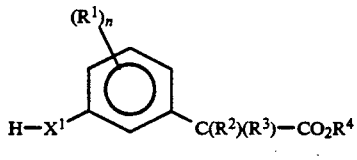

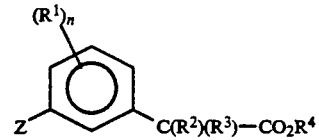

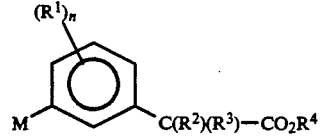

What we claim is:

1. An alkanoic acid derivative of the formula I

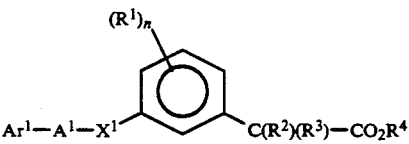

wherein $Ar^1$ is phenyl or naphthyl, or a 10-membered bicyclic heterocyclic moiety containing one or two nitrogen heteroatoms and optionally containing a further heteroatom selected from nitrogen, oxygen and sulphur, and $Ar^1$ may optionally bear up to four substituents selected from halogeno, hydroxy, cyano, oxo, thioxo, (1–4 C)alkyl (1–4 C)alkoxy, fluoro-(1–4 C)alkyl, phenyl, benzoyl, phenyl-(1–4 C)alkyl and α,α-difluorobenzyl, and wherein said phenyl substituent or any of said substituents which contain a phenyl group may optionally bear a substituent selected from halogeno, (1–4 C)alkyl and (1–4 C)alkoxy;

$A^1$ is a direct link to $X^1$ or is (1–3 C)alkylene;

$X^1$ is oxy, thio, sulphinyl or sulphonyl;

n is 0, 1 or 2, and $R^1$ is halogeno, (1–4 C)alkyl, (1–4 C)alkoxy or fluoro-(1–4 C)alkyl;

each of $R^2$ and $R^3$, which may be the same or different, is (1–4 C)alkyl, (2–4 C)alkenyl or (2–4 C)alkynyl; and $R^4$ is hydrogen or (1–4 C)alkyl;

or a pharmaceutically-acceptable salt thereof.

2. An alkanoic acid derivative of the formula I as claimed in claim 1 wherein $Ar^1$, $A^1$, $X^1$, $R^1$, n and $R^4$ have any of the meanings defined in claim 1 and wherein each of $R^2$ and $R^3$, which may be the same or different, is (1–4 C)alkyl, (2–4 C)alkenyl, (2–4 C)alkynyl or fluoro-(1–4 C)alkyl;

or a pharmaceutically-acceptable salt thereof.

3. An alkanoic acid derivative of the formula I as claimed in claim 1 wherein $Ar^1$ is phenyl which may optionally bear a substituent selected from fluoro, chloro, methyl, tert-butyl, phenyl, benzoyl, benzyl and α,α-difluorobenzyl and wherein said phenyl, benzoyl, benzyl or α,α-difluorobenzyl substituent may optionally bear a fluoro or chloro substituent, or $Ar^1$ is naphth-2-yl which may optionally bear a substituent selected from fluoro, chloro and methyl;

$A^1$ is a direct link to $X^1$, or is methylene;

$X^1$ is oxy, thio, sulphinyl or sulphonyl;

n is 0 or 1 and $R^1$ is from fluoro, chloro or trifluoromethyl;

each of $R^2$ and $R^3$, which may be the same or different, is methyl, ethyl, propyl, allyl or 2-propynyl;

$R^4$ is methyl, ethyl, propyl, butyl, or tert-butyl;

or a pharmaceutically-acceptable salt thereof.

4. An alkanoic acid derivative of the formula I as claimed in claim 1 wherein $Ar^1$ is 2-quinolyl, 6-quinolyl, 6-quinoxazinyl, 2-oxo-1,2-dihydroquinolin-3-yl, 2-oxo-1,2-dihydroquinolin-6-yl, 2-oxo-1,2-dihydroquinolin-7-yl, 3-oxo-2,3-dihydro-4 H-1,4-benzoxazin-7-yl or 3-oxo-2,3-dihydro-4 H-1,4-benzothiazin-7-yl, which may optionally bear one, two or three substituents selected from fluoro, chloro, methyl, ethyl and 2-fluoroethyl;

$A^1$ is a direct link to $X^1$, or is methylene;

$X^1$ is oxy, thio, sulphinyl or sulphonyl;

n is 0 or 1 and $R^1$ is fluoro, chloro or trifluoromethyl;

each of $R^2$ and $R^3$, which may be the same or different, is methyl, ethyl propyl, allyl or 2-propynyl;

and $R^4$ is methyl, ethyl, propyl, butyl or tert-butyl;

or a pharmaceutically-acceptable salt thereof.

5. An alkanoic acid derivative of the formula I as claimed in claim 1 wherein $Ar^1$ is 2-quinolyl, 6-quinolyl, 2-oxo-1,2-dihydroquinolin-3-yl or 2-oxo-1,2-dihydroquinolin-6-yl, which may optionally bear one substituent selected from fluoro, chloro, methyl and ethyl;

$A^1$ is a direct link to $X^1$, or is methylene;

$X^1$ is oxy, thio, sulphinyl or sulphonyl;

n is 0 or 1 and $R^1$ is fluoro, chloro or trifluoromethyl;

each of $R^2$ and $R^3$, which may be the same or different, is methyl, ethyl or allyl;

and $R^4$ is methyl or ethyl;

or a pharmaceutically-acceptable salt thereof.

6. An alkanoic acid derivative of the formula I as claimed in claim 1 wherein $Ar^1$ is naphth-2-yl, 2-quinolyl or 1-methyl-2-oxo-1,2-dihydroquinolin-6-yl;

$A^1$ is methylene and $X^1$ is oxy;

n is 0;

$R^2$ is methyl, ethyl or allyl;

$R^3$ is methyl or ethyl; and $R^4$ is methyl or ethyl;

or a pharmaceutically-acceptable salt thereof.

7. The alkanoic acid derivative of the formula I, or a pharmaceutically-acceptable salt thereof, as claimed in claim 1 selected from:

ethyl 2-ethyl-2-[3-(naphth-2-ylmethoxy)phenyl]butyrate, methyl 2-methyl-2-[3-(naphth-2-ylmethoxy)phenyl]propionate, ethyl 2-ethyl-2-[3-(2-quinolylmethoxy)phenyl]butyrate, ethyl 2-ethyl-2-[3-(1-methyl-2-oxo-1,2-dihydroquinolin-6-ylmethoxy)phenyl]butyrate, ethyl 2-methyl-2-[3-(1-methyl-2-oxo-1,2-dihydroquinolin-6-yl-methoxy)phenyl]butyrate and ethyl 2-allyl-2-[3-(1-methyl-2-oxo-1,2-dihydroquinolin-6-yl-methoxy)phenyl]butyrate.

8. A pharmaceutical composition which comprises an alkanoic acid derivative of the formula I, or a pharmaceutically-acceptable salt thereof, as claimed in any one of claims 1 to 7 in association with a pharmaceutically-acceptable diluent or carrier.

9. A method of treating a disease or medical condition mediated alone or in part by one or more leukotrienes which comprises administering to a warm-blooded animal requiring such treatment a 5-lipoxygenase-inhibitory amount of an alkanoic acid derivative of the formula I, or a pharmaceutically-acceptable salt thereof, as claimed in any one of claims 1 to 7.

* * * * *